United States Patent
Morel

[11] 4,293,500
[45] Oct. 6, 1981

[54] UNSATURATED ESTERS AND METHOD OF PREPARING THEM

[75] Inventor: Didier Morel, Lyon, France

[73] Assignee: Rhone-Poulenc Industries, Saint-Fons, France

[21] Appl. No.: 127,047

[22] Filed: Mar. 4, 1980

[30] Foreign Application Priority Data

Mar. 12, 1979 [FR] France ................. 79 06214

[51] Int. Cl.³ .......................................... C07C 67/28
[52] U.S. Cl. ......................................... 260/410.9 R
[58] Field of Search .............. 260/410.9 R, 410.9 M, 260/410.9 A

[56] References Cited

U.S. PATENT DOCUMENTS 3,981,907 9/1976 Hattori et al. .................. 260/488 H

OTHER PUBLICATIONS

Brieger, G. Chem. Absts. vol. 76, No. 94965n (1972).

Primary Examiner—John F. Niebling
Attorney, Agent, or Firm—Herbert F. Schwartz

[57] ABSTRACT

New esters are provided by reaction of an ester of the formula:

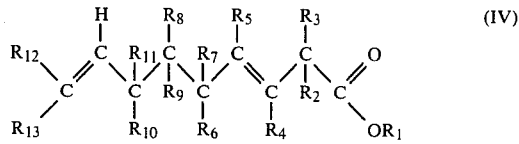

in the presence of a compound of rhodium and an alcohol with a 1,3-butadiene of the formula:

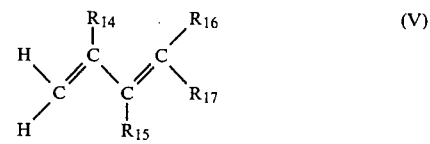

in which $R_1$ represents an alkyl radical having from about 1 to 6 carbons atoms, $R_2$, $R_3$, $R_5$, $R_8$ and $R_9$, which are identical or different, are a hydrogen atom or an alkyl radical having from about 1 to 3 carbon atoms.

$R_4$, $R_6$, and $R_7$ represent a hydrogen atom or an alkyl radical having from about 1 to 3 carbon atoms, at least one of them being a hydrogen atom, $R_{10}$, $R_{11}$, $R_{12}$, and $R_{13}$ represent a hydrogen atom or an alkyl radical having from about 1 to 3 carbon atoms, at least one of them being a hydrogen atom, $R_{14}$, $R_{15}$, $R_{16}$, and $R_{17}$, which are identical or different, each represents a hydrogen atom or an alkyl radical.

These new esters can be used as intermediates for the preparation of alcohols after hydrogenation and hydrogenolysis and for the preparation of soaps after hydrogenation and saponification.

15 Claims, No Drawings

UNSATURATED ESTERS AND METHOD OF PREPARING THEM

BACKGROUND OF THE INVENTION

The present invention relates to new unsaturated esters. More particularly, it concerns new $ACOOR_1$ esters in which the "A" group is a hydrocarbon group containing three double bonds. The invention also concerns a method of preparing these unsaturated esters.

Unsaturated esters of the formula R'COOB, in which it is the "B" group which contains three double bonds, are known from the prior art (French Pat. No. 71.02752, published under No. 2,007,072), corresponding U.S. Pat. No. 3,981,907. These esters can only be used as intermediates for the preparation of alcohols.

By the present invention, new esters have been discovered which can be used as intermediates for the preparation of alcohols after hydrogenation and hydrogenolysis and for the preparation of soaps after hydrogenation and saponification.

It is an object of the present invention to provide novel unsaturated esters which are useful as chemical intermediates.

It is also an object of the present invention to provide novel unsaturated esters useful as intermediates for the preparation of alcohols.

It is also an object of the present invention to provide a novel process for the preparation of the new esters of the invention.

Other objects will be apparent to those skilled in the art from the present specification.

GENERAL DESCRIPTION OF THE INVENTION

The new unsaturated esters of the present invention have the formula $ACOOR_1$, in which $R_1$ represents an alkyl group having from about 1 to 6 carbon atoms, and "A" is selected from among the group comprising hydrocarbon radicals of the formulae:

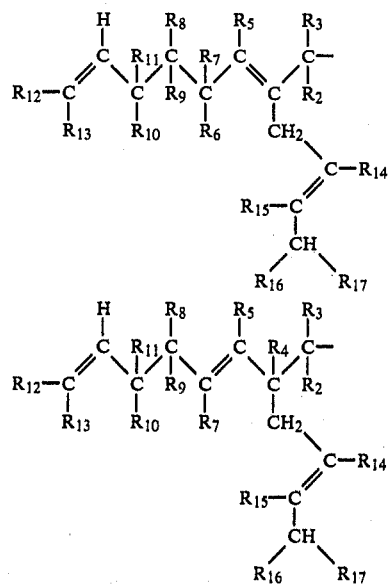

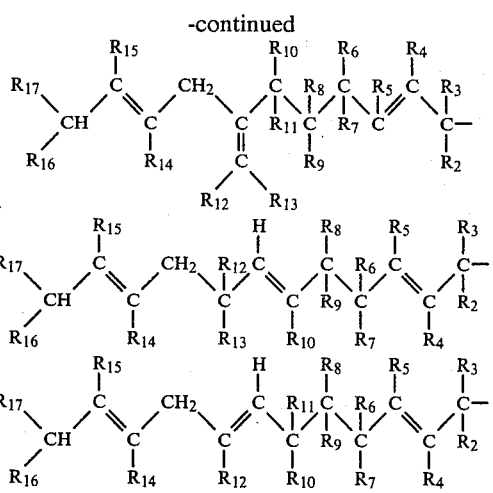

in which, $R_2$ to $R_{17}$, inclusive, are identical or different, and represent a hydrogen atom or an alkyl radical having from about 1 to 3 carbon atoms.

One particular object of the present invention is novel esters of the formulae:

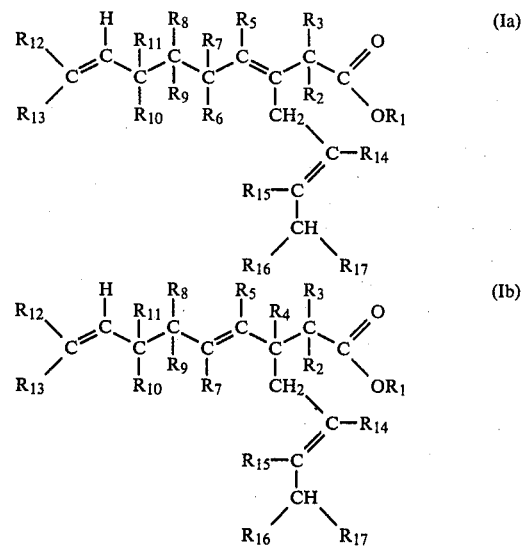

in which $R_1$ represents an alkyl radical having from about 1 to 6 carbon atoms, and $R_2$ to $R_{17}$, inclusive, which are identical or different, are a hydrogen atom or an alkyl radical having from about 1 to 3 carbon atoms.

More particularly, the invention concerns, among esters of formulae (Ia) and (Ib), above, the esters in which $R_1$ represents an alkyl radical having from about 1 to 4 carbon atoms and each of $R_2$ to $R_{17}$ represents a hydrogen atom.

Another preferred class of esters of the invention are esters of the formula:

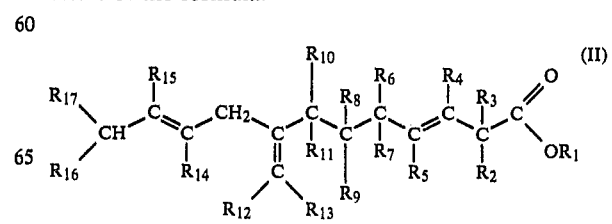

in which $R_1$ is an alkyl radical having from about 1 to 6 carbon atoms, and $R_2$ to $R_{17}$, inclusive, are identical or different, and are a hydrogen atom or an alkyl radical having from about 1 to 3 carbon atoms.

Among the esters of formula (II), above, the invention relates more particularly to those in which $R_1$ represents an alkyl radical having from about 1 to 4 carbon atoms and each of $R_2$ to $R_{17}$, inclusive, is a hydrogen atom.

Another preferred class of esters of the invention are those esters of the formulae:

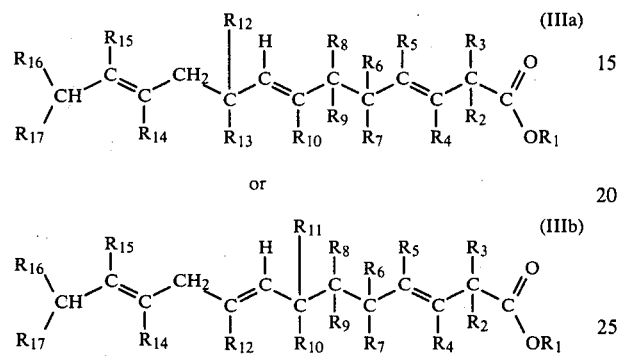

in which $R_1$ represents an alkyl radical having from about 1 to 6 carbon atoms, and $R_2$ to $R_{17}$, inclusive, which are identical or different, are a hydrogen atom or an alkyl radical having from about 1 to 3 carbon atoms.

Among the esters of formulae (IIIa) and (IIIb), above, the invention concerns more particularly those in which $R_1$ represents an alkyl radical having from about 1 to 4 carbon atoms and each of $R_2$ to $R_{17}$, inclusive, represents a hydrogen atom.

The invention also relates to a process of preparing compounds of formulae (Ia), (Ib), (II), (IIIa), and (IIIb), above, comprising reacting an ester of the formula:

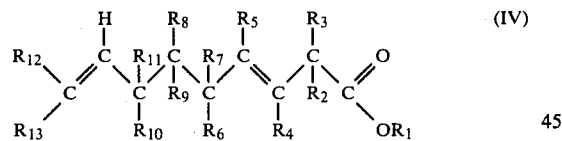

in which
$R_1$ represents an alkyl radical having from about 1 to 6 carbon atoms;
$R_2$, $R_3$, $R_5$, $R_8$, and $R_9$, which are identical or different, are a hydrogen atom or an alkyl radical having from about 1 to 3 carbon atoms;
$R_4$, $R_6$, and $R_7$ represent a hydrogen atom or an alkyl radical having from about 1 to 3 carbon atoms, at least one of them being a hydrogen atom;
$R_{10}$, $R_{11}$, $R_{12}$, and $R_{13}$ represent a hydrogen atom or an alkyl radical having from about 1 to 3 carbon atoms, at least one of them being a hydrogen atom;
with a 1,3-butadiene of the formula:

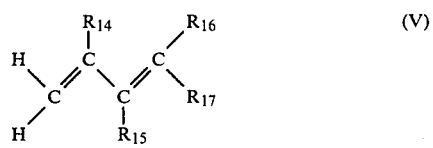

in which:

$R_{14}$, $R_{15}$, $R_{16}$, or $R_{17}$, which are identical or different, each represents a hydrogen atom or an alkyl radical, in the presence of a compound of rhodium and an alcohol.

The process of the invention is preferably carried out with the use of a compound of formula (IV), above, in which $R_1$ represents an alkyl radical having from about 1 to 4 carbon atoms and each of $R_2$ to $R_{13}$, inclusive, is a hydrogen atom.

Among these compounds of formula (IV) which are preferred are those of the formulae:

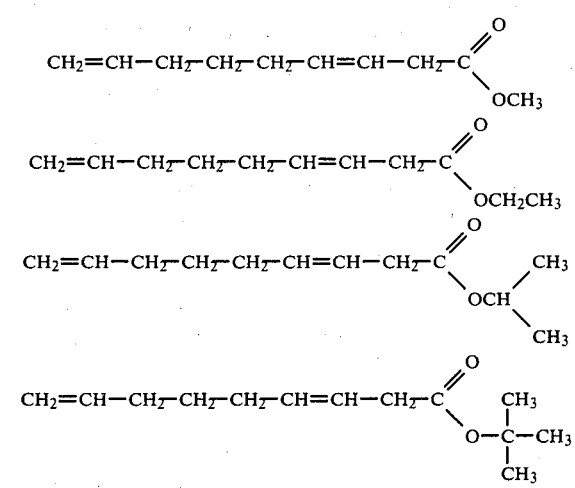

These are reacted with a compound of formula (V), above, in which $R_{14}$ to $R_{17}$, inclusive, are a hydrogen atom, that is to say, with 1,3-butadiene.

In accordance with the invention, it has surprisingly been found that when one uses, simultaneously with the said rhodium compound and the said alcohol, a trivalent compound of phosphorus, the formation of the ester of formula (II) is favored. The rhodium compound and the trivalent compound of phosphorus are preferably used in quantities such that the atomic ratio $$\frac{\text{trivalent phosphorus}}{\text{rhodium}}$$

is equal to or greater than 1.5. Still more preferably, this ratio is equal to about 3. By the present invention, it has also been found that the presence of the trivalent compound of phosphorus decreases the amount of heavy products formed (oligomers of butadiene and condensates of the compound of formula (IV), in particular).

When the trivalent compound of phosphorus is not added upon the carrying out of the reaction, the formation of compounds of formulae (I) and (III) are favored.

As the said alcohol there is preferably used an alcohol of formula R—OH in which R is an alkyl radical having from about 1 to 6 carbon atoms. Even more preferably, ethyl alcohol is employed.

The said rhodium compound is selected preferably from among the inorganic acid salts of rhodium. Among them, rhodium chloride, $RhCl_3$, is particularly preferred.

The trivalent compound of phosphorus is selected preferably from among the aryl and alkyl phosphines, such as, for instance, triphenyl phosphine and 1,2-bis(-diphenyl phosphino-)-ethylene of the formula:

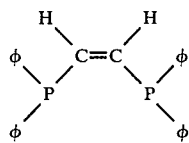
The molar ratio of the compound of formula (IV), above, to the rhodium compound is preferably between about 200 and about 2000, and the molar ratio of the said alcohol to the said rhodium compound is preferably between about 10 and about 100.
Among the compounds provided by the invention are those of the following formulae:
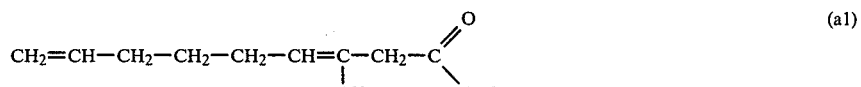 (a1)
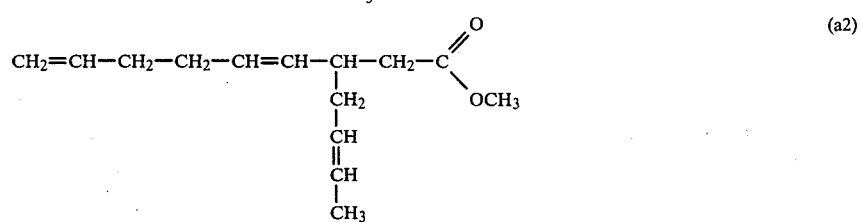 (a2)
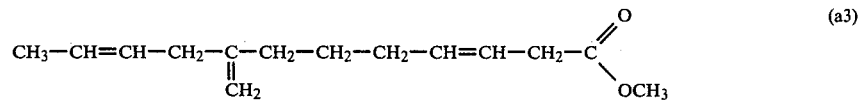 (a3)
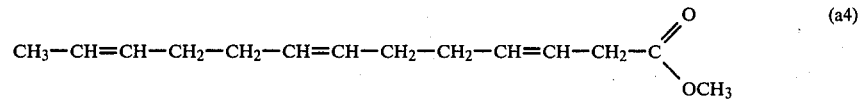 (a4)
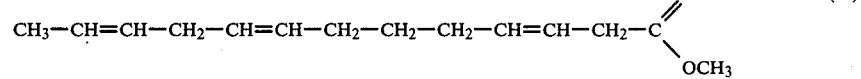 (a5)
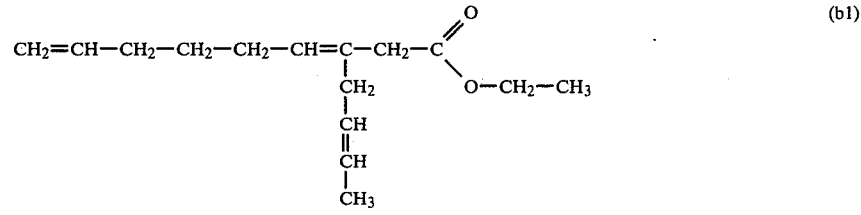 (b1)
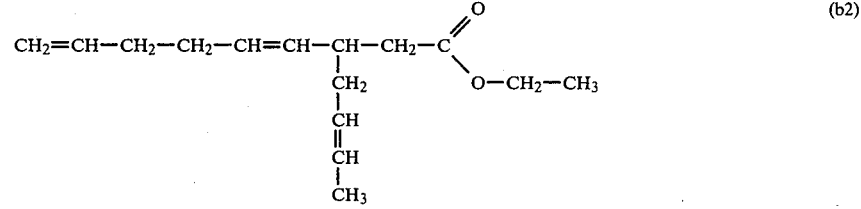 (b2)
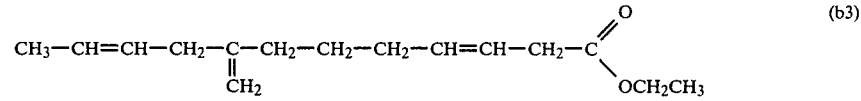 (b3)
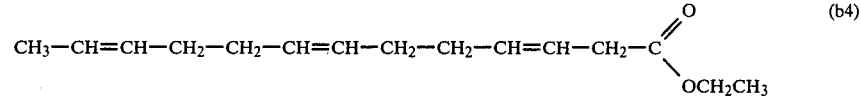 (b4)
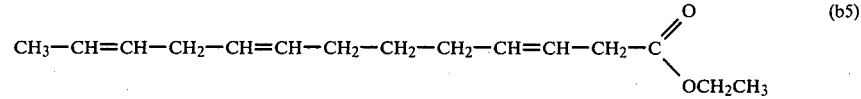 (b5)

-continued
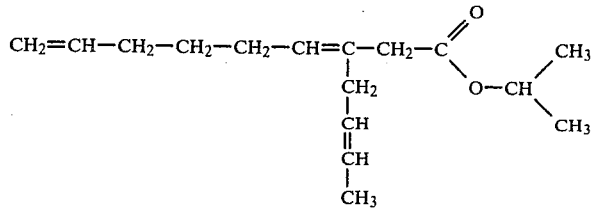  (c1)
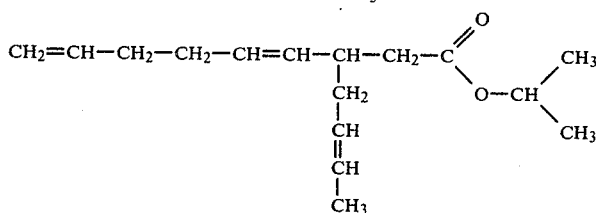  (c2)
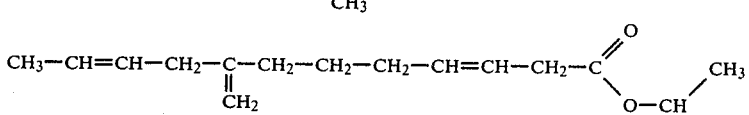  (c3)
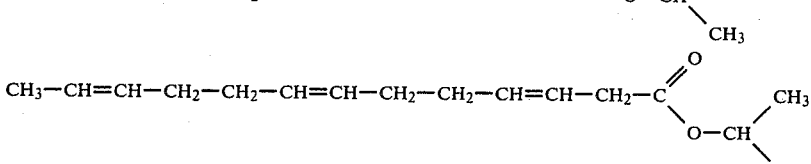  (c4)
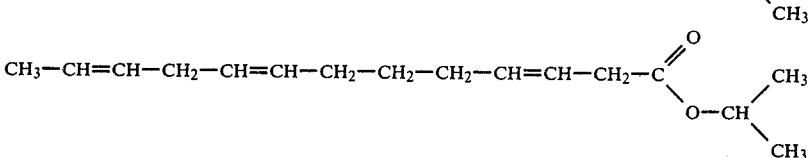  (c5)
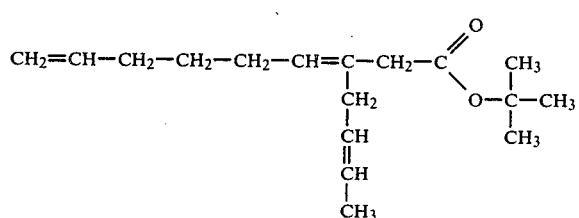  (d1)
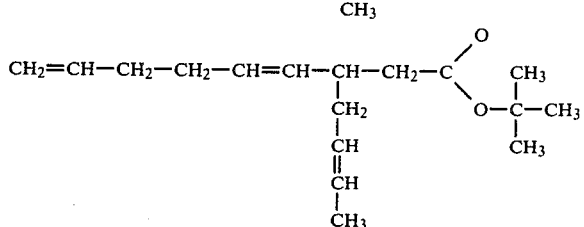  (d2)
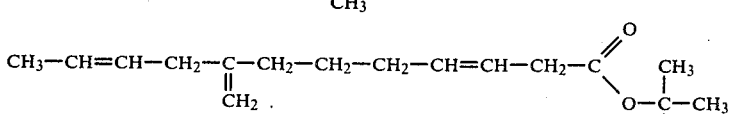  (d3)
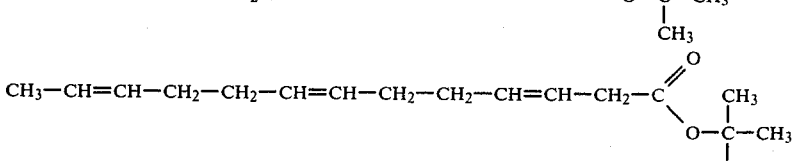  (d4)
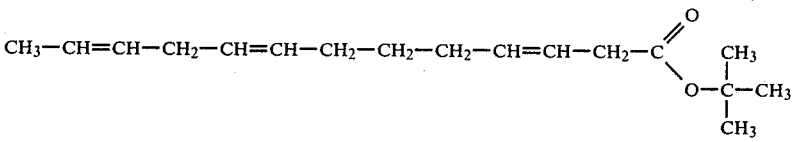  (d5)
The process of the invention is carried out at a temperature which is generally between about 90° C. and about 150° C. One preferably operates between about 100° C. and about 130° C.

The pressure employed is not a critical factor. One generally operates at atmospheric pressure, although a pressure less than or greater than atmospheric pressure presents no problems.

One generally operates in the following manner: A preferably stainless steel reactor is used, into which the reagents are introduced under an inert atmosphere, preferably, but not necessarily, in the following order: the said rhodium compound, trivalent compound of phosphorus (if the latter is used), said alcohol, compound of formula (IV), and compound of formula (V). The said alcohol, which is used in a small quantity, permits the activating of the catalytic system. Heating is effected with agitation. When the reaction is completed, the compound of formula (V) is eliminated by degasification. The products of the reaction are then isolated from the resultant mixture by distillation under reduced pressure.

The compounds of the invention can lead, either by hydrogenation of the olefin double bonds and saponification, to soaps, or, by hydrogenation and hydrogenolysis, to alcohols, which are precursors of biodegradable detergents.

The starting compounds of formula (IV) are prepared by prior art techniques. In particular, they can be prepared by reacting 1,3-butadiene in an alcohol under CO pressure in the presence of a catalytic system consisting of a palladium salt and triphenylphosphine at temperatures on the order of 110° C. [see for instance *Tetrahedron*, Vol. 28, page 3721 (1972)].

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

Reaction between ethyl-3,8-nonadienoate and 1,3-butadiene catalyzed by $RhCl_3$ and $C_2H_2OH$ without triphenylphosphine Into a 40 cc. glass tube, 0.043 g. (0.12 milligram atoms of Rh) of $RhCl_3 \times H_2O$ were introduced. The tube was closed by a rubber stopper (vaccine cap) and flushed three times by a vacuum-argon system. 0.3 g. (6.5 millimols) of ethanol, 16.32 g. (89.7 millimols of ethyl-3,8-nonadienoate and 5.22 g. (96.6 millimols) of 1,3-butadiene were added, one after the other. The tube was sealed and introduced into a 500 ml. autoclave which was heated at 120° C., with agitation, for 6½ hours.

The rate of conversion of the butadiene was 96.8 percent and that of the ethyl-3,8-nonadienoate was 76.5 percent.

The chromatographic coupling in vapor phase/mass spectrography, as well as the nuclear magnetic resonance of the proton and the infrared showed the presence of the expected products $b_1b_2b_3b_4b_5$ in the molar ratio $b_1+b_2:b_3:b_4+b_5$ equal to 33/2.5/64.5. More precisely, there were obtained:

2.72 g. of a mixture $b_1+b_2$
0.2 g. of $b_3$
5.33 g. of a mixture of $b_4+b_5$

EXAMPLE 2

Reaction between ethyl-3,8-nonadienoate and 1,3-butadiene catalyzed by $RhCl_3$ and $C_2H_5OH$ with triphenylphosphine (TPP)

Atomic ratio $(P+3)/Rh=3$.

0.043 g. of $RhCl_3 \times H_2O$ (0.12 milligram atom of Rh) and 0.097 g. (0.36 millimol) of TPP were introduced into a 40 cc. glass tube. The tube was closed by a rubber stopper (vaccine cap) and flushed three times in a vacuum-argon system. 0.39 g. (8.5 millimols) of ethanol, 15.8 g. (87 millimols) of ethyl-3,8-nonadienoate and 5.1 g. (94 millimols) of butadiene were introduced one after the other. The tube was sealed and introduced into a 500 ml. autoclave which is heated at 120° C., with agitation, for 6½ hours.

The conversion of the butadiene was 79 percent and that of the ethyl-3,8-nonadienoate was 39.2 percent.

By chromatographic analysis there were found the products $b_1b_2b_3b_4$ and $b_5$ in a molar ratio of $b_1+b_2:b_3:b_4+b_5=2/84/14$. More precisely, there were obtained:

0.13 g. of a mixture of $b_1+b_2$
5.83 g. of $b_3$
0.91 g. of a mixture of $b_4+b_5$ This example clearly shows that the addition of triphenylphosphine directs the reaction towards the formation of $b_3$ while decreasing the amount of the non-distillable heavy substances (3.5 percent in Example 2 instead of 30 percent in Example 1).

EXAMPLES 3 TO 5

The procedure of Example 2 was repeated, using the same starting products and the same catalytic system, but varying the atomic ratio $(P+3)/Rh$. The following results were obtained:

| | Starting Products | | | CR % | CR % | Products of the Reaction | | |
|---|---|---|---|---|---|---|---|---|
| | Ethyl-3,8-nonadienoate | butadiene | $\frac{p+3}{Rh}$ | butadiene | Ethyl-3,8-nonadienoate | $b_1+b_2$ | $b_3$ | $b_4+b_5$ |
| Ex. 3 | 16.7 g. | 5.22 g. | 1 | 98.3 | 74.3 | 2.48 g | 1.42 g | 2.48 g |
| Ex. 4 | 15.63 g. | 5.25 g. | 2 | 87.4 | 61.2 | 0.34 g | 8.03 g | 2.82 g |
| Ex. 5 | 15.78 g. | 5.58 g. | 6 | 71.5 | 30 | 0 | 4.90 g | 1.15 g |

CR = Conversion Rate

EXAMPLE 6

Reaction between isopropyl-3,8-nonadienoate and 1,3-butadiene catalyzed by $RhCl_3$ and $C_2H_5OH$ with triphenylphosphine The procedure of Example 2 was repeated, but using:
0.045 g. of $RhCl_3 \times H_2O$ (0.13 milligram atoms of Rh)
0.111 g. of triphenylphosphine (0.40 millimol)

0.18 g. of ethanol (3.9 millimols)
16 g. of isopropyl-3,8-nonadienoate (82 millimols)
5.3 g. of butadiene (98 millimols)

The conversion rate of the butadiene was 91 percent and that of the ispropyl-3,8-nonadienoate was 54 percent.

By chromatographic analysis there were found the compounds $c_1 c_2 c_3 c_4$ and $c_5$ in the molar ratio $c_1+c_2:c_3:c_4+c_5 = 5/71/26$. More precisely, there were obtained:

0.32 g. of a mixture of $c_1+c_2$
7.2 g. of $c_3$
2.65 g. of a mixture of $c_4+c_5$

EXAMPLES 7 AND 8

The procedure of Example 6 was followed repeated, but varying the atomic ratio $(P+3)/Rh$. The following results were obtained:

| | Starting Products | | | CR % | | Products of the Reaction | | |
|---|---|---|---|---|---|---|---|---|
| | Isopropyl-3,8-nona-dienoate | buta-diene | $\frac{p+3}{Rh}$ | CR % buta-diene | Isopropyl-3,8-nona-dienoate | $c_1+c_2$ | $c_3$ | $c_4+c_5$ |
| Ex. 6 | 16.2 g. | 4.9 g. | 0 | 98 | 66.5 | 2.24 g | 0.36 g | 5.89 g |
| Ex. 7 | 16.5 g. | 5.5 g. | 4 | 70.6 | 44.5 | 0.1 g | 7.62 g | 1.46 g |

CR = Conversion Rate

EXAMPLE 9

Reaction between tertibutyl-3,8-nonadienoate and 1,3-butadiene catalyzed by $RhCl_3$ and $C_2H_5OH$ with triphenylphosphine The procedure of Example 2 was repeated, but using:
0.045 g. of $RhCl_3$ (0.13 milligram atom of Rh)
0.111 g. of triphenylphosphine (0.40 millimol)
0.18 g. of ethanol (3.9 millimols)
17.4 g. of tertiobutyl-3,8-nonadienoate (83 millimols)
4.98 g. of butadiene (92 millimols)

The conversion rate of the butadiene was 73 percent and that of the tertiobutyl-3,8-nonadienoate was 48 percent.

By chromatographic analysis there were found the compounds $d_1 d_2 d_3 d_4$ and $d_5$ in the molar ratio $d_1+d_2:d_3:d_4+d_5 = 2/76/22$. More precisely, there were obtained:

0.18 g. of a mixture of $d_1+d_2$
7.5 g. of $d_3$
2.1 g. of a mixture of $d_4+d_5$

EXAMPLES 10 AND 11

The procedure of Example 9 was repeated, but varying the atomic ratio $(P+3)/Rh$. The following results were obtained:

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A mixture of unsaturated esters of the formula $ACOOR_1$, in which $R_1$ represents an alkyl group having from about 1 to 6 carbon atoms and "A" is selected from the group consisting of hydrocarbon radicals of the formulae:

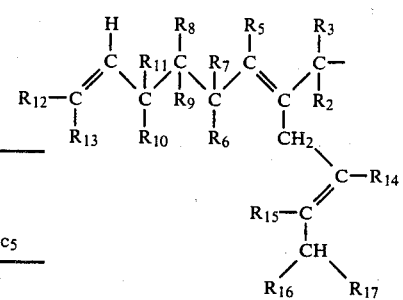

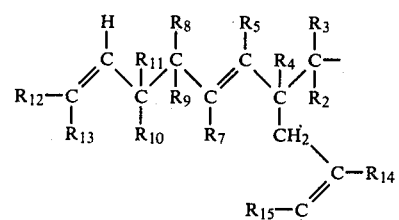

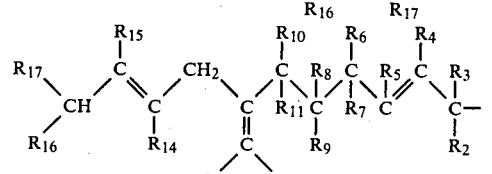

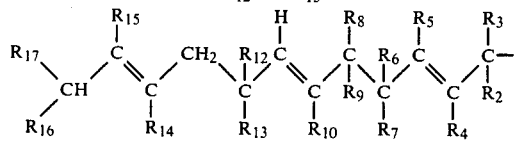

| | Starting Products | | | CR % | | Products of the Reaction | | |
|---|---|---|---|---|---|---|---|---|
| | Tertiobutyl-3,8-nonadien-oate | buta-diene | $\frac{p+3}{Rh}$ | CR % buta-diene | Tertiobutyl-3,8-nonadien-oate | $d_1+d_2$ | $d_3$ | $d_4+d_5$ |
| Ex. 10 | 18 g. | 5.4 g. | 0 | 89.5 | 83 | 4.65 g | 0.52 g | 7.96 g |
| Ex. 11 | 17.4 g. | 5.4 g. | 4 | 79 | 48.5 | 0.15 g | 7.5 g | 2.2 g |

CR = Conversion Rate

In Example 1, above, instead of $RhCl_3$, equivalent amounts of other inorganic salts of rhodium may be used, such as $Rh(NO_3)_3$, $Rh(SO_4)_3$, $Rh(SO_3)_3$, etc.

-continued

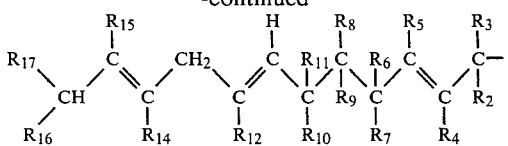

in which R₂ to R₁₇, inclusive, being identical or different, represent a member selected from the class consisting of a hydrogen atom and an alkyl radical having from about 1 to 3 carbon atoms, wherein said unsaturated ester in which hydrocarbon radical "A" has the formula:

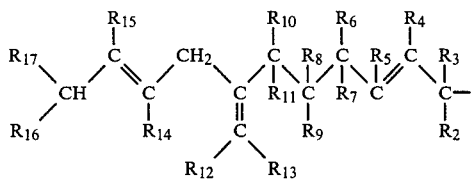

is the major component of said mixture.

2. An unsaturated ester, having the formula:

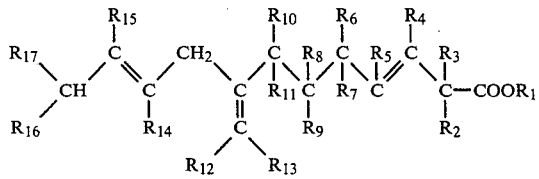

in which $R_1$ is an alkyl radical having from about 1 to 6 carbon atoms, and $R_2$ to $R_{17}$, inclusive, being identical or different, are a member of the class consisting of an atom of hydrogen or an alkyl radical having from about 1 to 3 carbon atoms.

3. An unsaturated ester according to claim 2, wherein in formula (II), $R_1$ represents an alkyl radical having from about 1 to 4 carbon atoms and each of $R_2$ to $R_{17}$, inclusive, represents a hydrogen atom.

4. A process of preparing a mixture of esters according to claim 1, comprising reacting an ester of the formula:

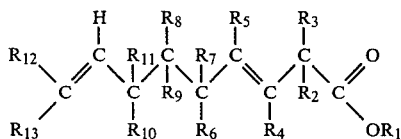

(IV)

in which:
R₁ represents an alkyl radical having from about 1 to 6 carbon atoms;
R₂, R₃, R₅, R₈, and R₉, being identical or different, are a member of the class consisting of a hydrogen atom or an alkyl radical having from about 1 to 3 carbon atoms;
R₄, R₆, and R₇ represent a hydrogen atom or an alkyl radical having from 1 to 3 carbon atoms, at least one of them being a hydrogen atom;

R₁₀, R₁₁, R₁₂, and R₁₃ represents a hydrogen atom or an alkyl radical having from 1 to 3 carbon atoms, at least one of them being a hydrogen atom,
with a 1,3-butadiene of the formula:

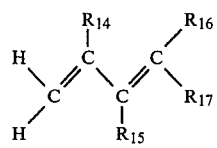

(V)

in which:
each of R₁₄, R₁₅, R₁₆, or R₁₇, being identical or different, represents a hydrogen atom or an alkyl radical, in the presence of a compound of rhodium, an alcohol and a trivalent compound of phosphorus, said trivalent compound of phosphorus being present in an amount such that the atomic ratio $$\frac{\text{trivalent phosphorus}}{\text{rhodium}}$$

is greater than or equal to about 1.5.

5. A process according to claim 4, wherein there are reacted an ester of formula (IV) in which R₁ represents an alkyl radical having from about 1 to 4 carbon atoms and each of R₂ to R₁₇, inclusive, represents a hydrogen atom, with a compound of formula (V) in which R₁₄ to R₁₇, inclusive, represent a hydrogen atom.

6. A process according to claim 4, wherein the atomic ratio $$\frac{\text{trivalent phosphorus}}{\text{rhodium}}$$

is equal to about 3.

7. A process according to claim 4, wherein the said trivalent compound of phosphorus is selected from the group consisting of aryl phosphines and alkyl phosphines.

8. A process according to claim 7, wherein the said trivalent compound of phosphorus is triphenylphosphine.

9. A process according to claim 4, wherein a compound of rhodium selected from among the inorganic salts of rhodium is used.

10. A process according to claim 9, wherein the compound of rhodium is rhodium chloride (RhCl₃).

11. A process according to claim 4, wherein the said alcohol has the formula ROH, in which R represents an alkyl radical having from about 1 to 6 carbon atoms.

12. A process according to claim 11, wherein the said alcohol is ethyl alcohol.

13. A process according to claim 4, wherein the molar ratio of the compound of formula (IV) to the compound of rhodium is between about 200 and 2000.

14. A process according to claim 4, wherein the molar ratio of the said alcohol to the compound of rhodium is between about 10 and about 100.

15. A process according to any of claims 4 to 14, wherein the temperature of the process is between about 90° C. and about 150° C.

* * * * *